US007196065B2

(12) United States Patent
Ernest

(10) Patent No.: US 7,196,065 B2
(45) Date of Patent: *Mar. 27, 2007

(54) ENTERAL FORMULATION

(76) Inventor: Stephen P. Ernest, 3285 N. Morning Star Ave., Sullivan, IN (US) 47882

( * ) Notice: Subject to any disclaimer, the term of this patent is extended or adjusted under 35 U.S.C. 154(b) by 201 days.

This patent is subject to a terminal disclaimer.

(21) Appl. No.: 10/992,985

(22) Filed: Nov. 19, 2004

(65) Prior Publication Data
US 2005/0070498 A1 Mar. 31, 2005

Related U.S. Application Data

(63) Continuation of application No. 10/468,931, filed as application No. PCT/US02/06595 on Mar. 5, 2002, now Pat. No. 6,864,242.

(60) Provisional application No. 60/273,498, filed on Mar. 5, 2001.

(51) Int. Cl.
*A61K 31/70* (2006.01)
*A61K 31/40* (2006.01)
*A61K 31/385* (2006.01)
*A61K 31/195* (2006.01)
*A61K 35/78* (2006.01)

(52) U.S. Cl. .................. 514/27; 514/423; 514/440; 514/560; 514/562; 514/563; 514/565; 514/675; 514/725

(58) Field of Classification Search .............. None
See application file for complete search history.

(56) References Cited

U.S. PATENT DOCUMENTS

| 4,020,158 A | 4/1977 | Ashmead |
| 4,158,057 A | 6/1979 | Stanko |
| 4,167,564 A | 9/1979 | Jensen |
| 4,308,257 A | 12/1981 | Caspe |
| 4,335,210 A | 6/1982 | Meister et al. |
| 4,351,835 A | 9/1982 | Stanko |
| 4,357,343 A | 11/1982 | Madsen et al. |
| 4,401,657 A | 8/1983 | Kashiwabara et al. |
| 4,415,575 A | 11/1983 | Bolhofer et al. |
| 4,427,658 A | 1/1984 | Maubois et al. |
| 4,434,158 A | 2/1984 | Meister et al. |
| 4,438,124 A | 3/1984 | Meister et al. |
| 4,526,793 A | 7/1985 | Ingenbleek et al. |
| 4,528,197 A | 7/1985 | Blackburn |
| 4,548,937 A | 10/1985 | Stanko |
| 4,599,152 A | 7/1986 | Ashmead |
| 4,647,571 A | 3/1987 | Meister et al. |
| 4,665,082 A | 5/1987 | Meister et al. |
| 4,752,618 A | 6/1988 | Mascioli et al. |
| 4,758,553 A | 7/1988 | Ogoshi |
| 4,774,089 A | 9/1988 | Ashmead |
| 4,784,685 A | 11/1988 | Meister |
| 4,830,716 A | 5/1989 | Ashmead |
| 4,847,296 A | 7/1989 | Babayan et al. |
| 4,863,898 A | 9/1989 | Ashmead et al. |
| 4,871,768 A | 10/1989 | Bistrian et al. |
| 4,874,790 A | 10/1989 | Stanko |
| 4,906,664 A | 3/1990 | Bistrian |
| 4,954,492 A | 9/1990 | Jensen |
| 4,981,687 A | 1/1991 | Fregly et al. |
| 4,981,844 A | 1/1991 | Alexander et al. |
| 4,994,442 A | 2/1991 | Gil et al. |
| 5,021,245 A | 6/1991 | Borschel et al. |
| 5,053,387 A | 10/1991 | Alexander |
| 5,055,446 A | 10/1991 | Alexander et al. |
| 5,059,622 A | 10/1991 | Sears |
| 5,066,500 A | 11/1991 | Gil et al. |
| 5,081,105 A | 1/1992 | Bistrian |
| 5,089,477 A | 2/1992 | Fregly et al. |
| 5,108,767 A | 4/1992 | Mulchandani et al. |
| 5,111,819 A | 5/1992 | Hurd |
| 5,116,819 A | 5/1992 | Trimbo et al. |
| 5,120,760 A | 6/1992 | Horrobin |
| 5,134,162 A | 7/1992 | Stanko |
| 5,147,650 A | 9/1992 | Fregly et al. |
| 5,166,189 A | 11/1992 | Trimbo et al. |
| 5,221,545 A | 6/1993 | Borschel et al. |
| 5,223,285 A | 6/1993 | DeMichele et al. |
| 5,230,902 A | 7/1993 | Gold et al. |
| 5,231,085 A | 7/1993 | Alexander et al. |
| 5,234,952 A | 8/1993 | Crozier-Willi et al. |
| 5,236,712 A | 8/1993 | Fregly et al. |
| 5,238,684 A | 8/1993 | Fregly et al. |
| 5,256,697 A | 10/1993 | Miller et al. |
| 5,262,406 A | 11/1993 | Vitale |

(Continued)

FOREIGN PATENT DOCUMENTS

EP 265 699 A2 5/1988

(Continued)

OTHER PUBLICATIONS

Medline Abstract No. 97217050, Kumar, Indian Journal of Experimental Biology, (May 1996) 34(5), 391-402.*

(Continued)

*Primary Examiner*—Raymond J. Henley, III
(74) *Attorney, Agent, or Firm*—Barnes & Thornburg LLP

(57) ABSTRACT

A formulation for enteral administration to a patient is disclosed.

19 Claims, No Drawings

U.S. PATENT DOCUMENTS

| | | | |
|---|---|---|---|
| 5,283,260 A | 2/1994 | Miller et al. | |
| 5,290,571 A | 3/1994 | Bounous et al. | |
| 5,294,641 A | 3/1994 | Stanko | |
| 5,403,826 A | 4/1995 | Cope et al. | |
| 5,438,042 A | 8/1995 | Schmidl et al. | |
| 5,444,054 A | 8/1995 | Garleb et al. | |
| 5,451,412 A | 9/1995 | Bounous et al. | |
| 5,456,924 A | 10/1995 | Bounous et al. | |
| 5,457,130 A | 10/1995 | Tisdale et al. | |
| 5,470,839 A | 11/1995 | Laughlin et al. | |
| 5,480,872 A | 1/1996 | Cope et al. | |
| 5,488,039 A | 1/1996 | Masor et al. | |
| 5,492,899 A * | 2/1996 | Masor et al. | 514/47 |
| 5,492,938 A | 2/1996 | Kyle et al. | |
| 5,504,072 A | 4/1996 | Schmidl et al. | |
| 5,545,668 A | 8/1996 | Skubitz et al. | |
| 5,547,927 A | 8/1996 | Cope et al. | |
| 5,549,905 A | 8/1996 | Mark et al. | |
| 5,571,783 A | 11/1996 | Montagne et al. | |
| 5,576,287 A | 11/1996 | Zaloga et al. | |
| 5,576,351 A | 11/1996 | Yoshimura et al. | |
| 5,578,576 A | 11/1996 | Leddin | |
| 5,583,159 A | 12/1996 | Horrobin et al. | |
| 5,589,468 A | 12/1996 | Lin et al. | |
| 5,602,109 A | 2/1997 | Masor et al. | |
| 5,612,060 A | 3/1997 | Alexander | |
| 5,635,199 A | 6/1997 | Trimbo et al. | |
| 5,646,005 A | 7/1997 | Kudsk | |
| 5,656,588 A | 8/1997 | Zaloga et al. | |
| 5,656,608 A | 8/1997 | Schneider et al. | |
| 5,658,895 A | 8/1997 | Aoi et al. | |
| 5,661,123 A | 8/1997 | Stalker et al. | |
| 5,661,180 A | 8/1997 | DeMichele et al. | |
| 5,663,202 A | 9/1997 | Horrobin et al. | |
| 5,670,157 A | 9/1997 | Trimbo et al. | |
| 5,670,540 A | 9/1997 | Horrobin et al. | |
| 5,686,429 A | 11/1997 | Lin et al. | |
| 5,691,320 A | 11/1997 | Von Borstel et al. | |
| 5,700,590 A | 12/1997 | Masor et al. | |
| 5,700,782 A | 12/1997 | Cope et al. | |
| 5,712,256 A | 1/1998 | Kulkarni et al. | |
| 5,714,472 A | 2/1998 | Gray et al. | |
| 5,719,134 A | 2/1998 | Schmidl et al. | |
| 5,723,446 A | 3/1998 | Gray et al. | |
| 5,728,678 A | 3/1998 | Trimbo et al. | |
| 5,731,290 A | 3/1998 | Schneider | |
| 5,731,346 A | 3/1998 | Egberg et al. | |
| 5,733,884 A | 3/1998 | Barbul et al. | |
| 5,747,459 A | 5/1998 | Rowe et al. | |
| 5,747,533 A | 5/1998 | Egberg et al. | |
| 5,756,481 A | 5/1998 | Arnal et al. | |
| 5,780,237 A | 7/1998 | Bursten et al. | |
| 5,780,451 A | 7/1998 | DeMichele et al. | |
| 5,817,695 A | 10/1998 | Pellico | |
| 5,821,217 A | 10/1998 | Forse et al. | |
| 5,824,693 A | 10/1998 | Goldberg | |
| 5,849,324 A | 12/1998 | Dohnalek et al. | |
| 5,849,335 A | 12/1998 | Ballevre et al. | |
| 5,863,906 A | 1/1999 | Arnal et al. | |
| 5,871,769 A | 2/1999 | Fleming et al. | |
| 5,874,471 A | 2/1999 | Waugh | |
| 5,886,037 A | 3/1999 | Klor et al. | |
| 5,888,552 A | 3/1999 | Bounous et al. | |
| 5,888,553 A | 3/1999 | Grant et al. | |
| 5,889,040 A | 3/1999 | Beale et al. | |
| 5,902,578 A | 5/1999 | Dohnalek et al. | |
| 5,902,829 A | 5/1999 | Schneider et al. | |
| 5,916,921 A | 6/1999 | Nishihira et al. | |
| 5,919,822 A | 7/1999 | Cotter et al. | |
| 5,922,766 A | 7/1999 | Acosta et al. | |
| RE36,288 E | 8/1999 | Lin et al. | |
| 5,952,295 A | 9/1999 | Arnaud-Battandier et al. | |
| 5,952,314 A | 9/1999 | DeMichele et al. | |
| 5,962,712 A | 10/1999 | DeMichele et al. | |
| 5,968,896 A | 10/1999 | Bell et al. | |
| 5,989,231 A | 11/1999 | Snow et al. | |
| 5,993,221 A | 11/1999 | Bistrian | |
| 6,001,878 A | 12/1999 | Van Leeuwen et al. | |
| 6,007,808 A | 12/1999 | De Haen et al. | |
| 6,013,273 A | 1/2000 | Schneider et al. | |
| 6,013,665 A | 1/2000 | DeMichele et al. | |
| 6,028,107 A | 2/2000 | Waugh | |
| 6,036,992 A | 3/2000 | Borror et al. | |
| 6,043,259 A | 3/2000 | Dhalla et al. | |
| 6,048,543 A | 4/2000 | Schneider et al. | |
| 6,060,269 A | 5/2000 | Chatterton et al. | |
| 6,060,446 A | 5/2000 | Zaloga et al. | |
| 6,066,112 A | 5/2000 | Quinn | |
| 6,069,168 A | 5/2000 | Horrobin et al. | |
| 6,077,828 A | 6/2000 | Abbruzzese et al. | |
| 6,080,787 A | 6/2000 | Carlson et al. | |
| 6,107,334 A | 8/2000 | Chilton | |
| 6,139,900 A | 10/2000 | Foegeding et al. | |
| 6,146,670 A | 11/2000 | Prieto et al. | |
| 6,160,007 A | 12/2000 | DeMichele et al. | |
| RE37,020 E | 1/2001 | Lin et al. | |
| 6,180,099 B1 | 1/2001 | Paul | |
| 6,180,671 B1 | 1/2001 | Freedman et al. | |
| 6,194,379 B1 | 2/2001 | McEwen et al. | |
| 6,200,624 B1 | 3/2001 | Mazer et al. | |
| 6,204,244 B1 | 3/2001 | Schneider | |
| 6,210,700 B1 | 4/2001 | Valente et al. | |
| 6,214,373 B1 | 4/2001 | Snowden | |
| 6,221,423 B1 | 4/2001 | Cho et al. | |
| 6,231,549 B1 | 5/2001 | Noecker et al. | |
| 6,241,983 B1 | 6/2001 | Paul et al. | |
| 6,245,803 B1 | 6/2001 | Acosta et al. | |
| 6,248,909 B1 | 6/2001 | Akimoto et al. | |
| 6,258,387 B1 | 7/2001 | McEwen et al. | |
| 6,281,244 B1 | 8/2001 | Schneider et al. | |
| 6,288,116 B1 | 9/2001 | Lowry et al. | |
| 6,300,950 B1 | 10/2001 | Clark et al. | |
| 6,313,273 B1 | 11/2001 | Thomas et al. | |
| 6,322,495 B1 | 11/2001 | Snow et al. | |
| 6,326,000 B1 | 12/2001 | Vesely et al. | |
| 6,326,031 B1 | 12/2001 | Hsia et al. | |
| 6,326,355 B1 | 12/2001 | Abbruzzese et al. | |
| 6,864,242 B2 * | 3/2005 | Ernest | 514/27 |
| 2001/0016214 A | 9/1999 | Kanauchi | |
| 2001/0007878 A1 | 7/2001 | Lowry et al. | |
| 2001/0018066 A1 | 8/2001 | Hahn | |
| 2001/0020007 A1 | 9/2001 | Wiss | |
| 2001/0022980 A1 | 9/2001 | Bell et al. | |
| 2001/0043958 A1 | 11/2001 | McEwen et al. | |
| 2001/0047036 A1 | 11/2001 | Vanderhoof et al. | |
| 2001/0049352 A1 | 12/2001 | Mark et al. | |

FOREIGN PATENT DOCUMENTS

EP    0 560 989 A1    9/1993

OTHER PUBLICATIONS

Medline Abstract No. 96432582, Oka et al., Japanese Journal of Pharmacology, (Jun. 1996) 71(2), 89-100.*
Medline Abstract No. 97074593, Smith et al., CA: A Cancer Journal for Clinicians, (Nov.-Dec. 1996), 46(6), 343-63.*
Medline Abstract No. 1998029329, Rickels et al., Journal of Clinical Psychiatry, (1997) 58 Suppl. 11, 44-10.*
Novartis Nutrition Corporation (Novartis Medical Nutrition), "Novartis Nutrition Pocket Guide", Jan. 2004, pp. 1-180.
NestléClinical Nutrition, "NestléClinical Nutrition Product Guide", Jul. 2002, pp. 1-80.
Mead Johnson & Company (Mead Johnson Nutrition), "Medical Nutritions Guide", Jan. 2001, pp. 1-80.

Novartis Nutrition Coporation (Novartis Medical Nutrition), "Your Source Chart—Product Reference Guide", Apr. 2004, pp. 1-55.

Merck & Co., Inc., "The Merck Index—An Encyclopedia of Chemicals, Drugs, and Biologicals", Eleventh Edition, 1989, 2 pgs.

O. Horakova et al., Abstract of "Presence of .alpha.-lipoic acid in natural raw materials", 1964, vol. 13, No. 3, pp. 107-110.

Perspectives in Practice, "Alternative lipid sources for enteral and parental nutrition: Long- and medium-chain triglycerides, structured triglycerides, and fish oils", Jan. 1991, vol. 91, No. 1, pp. 74-78.

Journal of the American Oil Chemists' Society, "Interesterification of Fats", Nov. 1978, pp. 796-805.

Webpage from Abbott Laboratories Online obtained through Ross.com, "Product Handbook for Advera", printed Jun. 16, 2004 at 11:12 p.m., 7 pgs.

Webpage from Abbott Laboratories Online obtained through Ross.com, "Product Handbook for AlitraQ", printed Jun. 16, 2004 at 11:52 p.m., 9 pgs.

Webpage from Abbott Laboratories Online obtained through Ross.com, "Product Handbook for Ensure", printed Jun. 16, 2004 at 11:19 p.m., 6 pgs.

Webpage from Abbott Laboratories Online obtained through Ross.com, "Product Handbook for Glucerna", printed Jun. 16, 2004 at 11:25 p.m., 9 pgs.

Webpage from Abbott Laboratories Online obtained through Ross.com, "Product Handbook for Hi-Cal", printed Jun. 16, 2004 at 11:29 p.m., 4 pgs.

Webpage from Abbott Laboratories Online obtained through Ross.com, "Product Handbook for Introlite", printed Jun. 16, 2004 at 11:33 p.m., 6 pgs.

Webpage from Abbott Laboratories Online obtained through Ross.com, "Product Handbook for Jevity 1 Cal", printed Jun. 16, 2004 at 11:41 p.m., 7 pgs.

Webpage from Abbott Laboratories Online obtained through Ross.com, "Product Handbook for Jevity 1.5 Cal", printed Jun. 16, 2004 at 11:46 p.m., 8 pgs.

Webpage from Abbott Laboratories Online obtained through Ross.com, "Product Handbook for Nepro", printed Jun. 16, 2004 at 11:51 p.m., 8 pgs.

Webpage from Abbott Laboratories Online obtained through Ross.com, "Product Handbook for NutriFocus", printed Jun. 16, 2004 at 11:57 p.m., 5 pgs.

Webpage from Abbott Laboratories Online obtained through Ross.com, "Product Handbook for Optimental", printed Jun. 17, 2004 at 12:03 a.m., 6 pgs.

Webpage from Abbott Laboratories Online obtained through Ross.com, "Product Handbook for Osmolite", printed Jun. 17, 2004 at 12:05 a.m., 8 pgs.

Webpage from Abbott Laboratories Online obtained through Ross.com, "Product Handbook for Pulmocare", printed Jun. 17, 2004 at 12:38 a.m., 11 pgs.

Webpage from Abbott Laboratories Online obtained through Ross.com, "Product Handbook for Osmolite 1.2 Cal", printed Jun. 17, 2004 at 12:12 a.m., 7 pgs.

Webpage from Abbott Laboratories Online obtained through Ross.com, "Product Handbook for Oxepa", printed Jun. 17, 2004 at 12:15 a.m., 10 pgs.

Webpage from Abbott Laboratories Online obtained through Ross.com, "Product Handbook for Perative", printed Jun. 17, 2004 at 12:33 a.m., 7 pgs.

Webpage from Abbott Laboratories Online obtained through Ross.com, "Product Handbook for Promote", printed Jun. 17, 2004 at 12:28 a.m., 6 pgs.

Webpage from Abbott Laboratories Online obtained through Ross.com, "Product Handbook for ProSure", printed Jun. 17, 2004 at 12:34 a.m., 8 pgs.

Webpage from Abbott Laboratories Online obtained through Ross.com, "Product Handbook for Suplena", printed Jun 17, 2004 at 12:42 a.m., 7 pgs.

Webpage from Abbott Laboratories Online obtained through Ross.com, "Product Handbook for TwoCal HN", printed Jun. 17, 2004 at 12:47 a.m., 5 pgs.

Webpage from Abbott Laboratories Online obtained through Ross.com, "Product Handbook for Vital HN", printed Jun. 17, 2004 at 12:51 a.m., 9 pgs.

International Search Report for PCT Application No. PCT/US02/06595, May 29, 2002, 4 pgs.

Ohnishi, S. T. et al.; "Sickle-cell anemia: a potential nutritional approach for a molecular disease," US National Library of Medicine (NLM), Bethesda, MD, US, May 2000 XP-002286604 Database Medline.

Jain, K. K.; "Pathophysiology and pharmacotherapy of chronic venous insufficiency: A critical Review" Journal of Clinical Research, 1998, GB, XPChemistry, vol. 13, No. 6, pp. 1200-1210, XP002286605.

Production description of NutriVir™ published by BIOnexus, no date available.

* cited by examiner

ENTERAL FORMULATION

CROSS-REFERENCE TO RELATED APPLICATIONS

This patent application is a continuation of U.S. patent application Ser. No. 10/468,931, filed Aug. 22, 2003, now issued U.S. Pat. No. 6,864,242 B2, which is a U.S. national counterpart application of international application Ser. No. PCT/US02/06595 filed Mar. 5, 2002, which claims the benefit under 35 U.S.C. § 119(e) of U.S. provisional patent application Ser. No. 60/273,498 filed on Mar. 5, 2001, which is incorporated herein by reference.

TECHNICAL FIELD OF THE INVENTION

The present invention generally relates to a formulation for enteral administration to a patient.

BACKGROUND OF THE INVENTION

The present invention generally relates to a formulation for enteral administration to a patient.

A broad population of patients require increased nutrients and energy as a result of suffering from various diseases or insults. For example, patients suffering from traumatic injury, burns, post-surgery, and some disease states have a significant need for increased nutrients and energy as compared to individuals who are not challenged by such metabolic stress.

In fact, non-essential nutrients and substances that a patient's body can typically synthesize in adequate supply, may become limiting when challenged by a metabolic stress. Furthermore, absorption of nutrients from the gut can be compromised even when there is no direct injury to the gastrointestinal system.

Accordingly, patients faced with such metabolic challenges are fed either with parenteral formulations or enteral formulations either to replace or supplement a typical diet. For example, in 1991, of an estimated 2.4 million trauma patients in the United States, 13% (310,000) required nutrition support beyond food. Of these patients, 62% of the patients were supported using enteral nutrition, 70% tube-feeding, and 30% oral supplements, while 38% were initially supported using parenteral nutrition and progressed to tube-feeding, if they survived. Similarly, of about 106,000 burn patient admissions in 1991 in the U.S., approximately 20% (21,000) required nutritional support. Of this group, 95% were started on enteral nutrition, 70% began on tube feeding and 30% started on oral supplements.

Numerous enteral formulations have been targeted for metabolically challenged patients. These products include: Mead-Johnson's Magnacal, Traumacal, and Isocal; Ross's Ensure Plus, Ensure, and Osmolite; and Novartis's Precision Isotein HN. Although such products are used in an attempt to treat and/or provide nutritional requirements, a drawback to these formulations is that they fall short in meeting some of the needs of metabolically challenged patients. Accordingly, there is a need for an enteral formulation which satisfies a greater number of the needs of the metabolically challenged patient.

SUMMARY OF THE INVENTION

In accordance with one embodiment of the present invention, there is provided a formulation for enteral administration to a patient. The formulation includes from about 1 gram to about 5 grams of Arginine per 240 calories of the formulation. The formulation also includes from about 1.5 grams to about 7.5 grams of glutamine per 240 calories of the formulation. In addition, the formulation includes from about 1 gram to about 5.5 grams of Proline per 240 calories of the formulation. The formulation also includes from about 2.4 grams to about 9 grams of branched chain amino acids per 240 calories of the formulation.

In accordance with another embodiment of the present invention, there is provided a formulation for enteral administration to a patient. The formulation includes Pycnogenol, Alpha-Lipoic acid, Oxerutin, a triterpene glycoside, Coenzyme Q10, and N-acetyl-cysteine.

In accordance with still another embodiment of the present invention there is provided a formulation for enteral administration to a patient. The formulation includes a first triglyceride containing two eicosapentaenoic acid residues. The formulation also includes a second triglyceride containing two gamma-linolenic acid residues.

DETAILED DESCRIPTION OF THE PREFERRED EMBODIMENT

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

An enteral formulation (hereinafter referred to as the formula) designed to meet the nutritional needs of patients suffering from a number of metabolic challenges is described herein. The formula is further designed to meet the needs of patients with varying fluid and caloric requirements (from 0.6 kcal/ml to 3.1 kcal/ml). The formula is further designed to prevent and treat multiple different diseases, including, but not limited to, the following:

| | | |
|---|---|---|
| Diarrhea/Nausea | Malabsorption/ GI Impairment | Crohn's |
| IBD | Ulcerative colitis | Bowel Resection |
| Irradiated Bowel | Pancreatitis | Glomerulonephritis |
| Immunosuppression | Metabolic Stress | Critically ill/hypermetabolic |
| Pulmonary disease | ARDS, COPD | Thrombosis |
| Increased TNF (tumor necrosis factor) | Ventilator Dependent | |
| Respiratory Failure | Pneumonia | Infection |
| Sepsis/SIRS | Hypoperfusion | Endotoxic shock |
| Multiple Organ Failure | DIC/Symptoms | Abscesses |
| Surgery | Trauma | HIV/AIDS/ARC |
| Cancer Radiation/Chemotherapy | Cachexia/Anorexia | |
| Wounds/Decubiti | Burns | Diabetes mellitus (I/N DDM) |
| Stress hyperglycemia | Renal dysfunction | Liver dysfunction |
| Transitional feeding | Long Term feeding | Hypoalbuminemia |
| Coronary Artery disease | CHF | Cardiogenic shock |
| CVA | CNS/Radiation damage | |
| Ischemic repurfusion injury | Venous insufficiency | Gangrene |
| Amputation | Adaptable to renal and/or hepatic failure | Anemia |

The formula is further designed to restore organ function toward optimal function, including the heart, lungs, liver, kidneys, gastrointestinal tract, skin, muscle, circulation, nervous system, and blood vessels. In addition, the formula is further designed to build up the body from the inside out: improve albumin levels, improve lean muscle mass, decrease risk of thrombosis while improving blood vessel strength and integrity, and improving overall cellular function and energy utilization. The formula is further designed to reduce time and cost of clinical response and rehabilitation in addition to reducing mortality and morbidity. The formula also increases the absorption of specific ingredients, while minimizing the diarrhea commonly associated with such ingredients.

Note that the formula is designed to provide ingredients as a concentration per 240 calories, and thus adaptable to any caloric concentration desired.

As used herein the terms Long Chain Triglyceride (LCT) means a glycerol backbone with 2 or 3, usually 3, long chain fatty acids attached; Omega 3 fatty acids primarily include, but are not limited to, EPA (Eicosapentaenoic acid, 20:5n3) DHA (Docosahexaenoic acid, 22:6n3), STA (Stearidonic acid (18:4n3), DPA (Docosapentaenoic acid, 22:4n3), ETA (Eicosatetraenoic acid, 20:4n3), ALA (Alpha-linolenic acid, 18:3n3), Omega 6 fatty acids include, but are not limited to GLA (Gamma-linolenic acid, 18:3n6), DGLA (dihomo-gammalinolenic acid 20:3n6), LA (Alpha Linoleic acid; 18:3n6); Medium Chain Triglyceride (MCT) means a glycerol backbone, with 2 or 3, usually 3, medium chain fatty acids attached; Medium Chain Fatty Acids (MCFAs), include, but are not limited to Caproic (6:0), Capyrlic (8:0), Capric (10:0), Lauric (12:0); and Monounsaturated Fatty acids (MUFAs), include, but are not limited to Oleic (18:1n9), Eicosanoic (20:1n9), and Erucic (22:1n9).

The formula contains a lipid blend, that includes structured Lipids, MCTs, and MUFAs. Preferably, the formula contains less than about 25% Linoleic Acid (LA), preferably, less than about 15%, and most preferably less than about 10% Linoleic Acid (by total fat calories). The structured lipid blend of the formula can contain, per 240 calories, GLA/DGLA at a range of about 0.1–to about 4.0 gm, preferably about 0.7–to about 1.2 gm, most preferably about 0.85 gm of GLA/DGLA.

The structured lipid blend further contains, per 240 calories, an Omega 3 Fatty acid chosen from the group EPA, DHA, STA, DPA, and/or ETA, at a range of about 0.5 to about 7.0 gm, preferably about 1.0–to about 2.0 gm, most preferably about 1.4 gm. In regards to the structured lipid, two residues of GLA are preferred for one of the structured lipids and two residues of EPA for another structured lipid. In addition, DHA can be utilized as two of the residues of the structured lipid.

In regards to the structured lipids, if EPA is combined with other fatty acids, the weight ratio of EPA to other fatty acids is at least 2:1. In regards to the structured lipid, by weight, GLA is at least 30% less than the total Omega 3 Fatty Acids chosen. It should be appreciated that, Alpha Linolenic acid is excluded from the structured lipids. In addition, if EPA and DHA are utilized on the structured lipid, GLA will not exceed EPA (by weight). If EPA is used alone on a structure lipid in the formula, then GLA in the formula will be at least 30% less than EPA (by weight).

It is preferable that the formula contains a structured lipid which contains 1 MCFA as one residue while the other two residues will contain either GLA or an Omega 3 fatty acid. With respect to GLA, it should be understood that DGLA can be substituted therefore, however GLA is preferred. With respect to the aforementioned MCFA it will be chosen from the following group: Caproic, Caprylic, Capric, and/or Lauric acids, or mixtures thereof. In addition, it is preferred that one structured lipid will have solely GLA as the second and third residue. In addition, it is preferred that one structured lipid will have solely the chosen Omega 3 fatty acid.

The chosen structured lipids can be combined into a structured lipid blend which can provide specific dosages and ratios of GLA and the chosen Omega 3 fatty acid, per 240 calories. With respect to the structured lipid blend, it contains natural (fractionated/purified) MCTs and MUFAs, and MCTs provide at least about 10% of the remaining fat calories needed per 240 calories, preferably at least about 25%, and most preferably about 40–to about 70% of the remaining fat calories. With respect to MUFAs, they are to provide at least about 10% of the remaining fat calories needed per 240 calories, preferably at least about 25%, and most preferably about 30–to about 68% of the remaining fat calories.

The structured glycerides of this invention may be prepared by any procedure commonly used to make structured lipids. For example, an interesterification or transesterification reaction made by mixing oils, or selective fractions of the oils, in stoichiometric proportions and then causing the transesterification reaction to proceed using catalysts or enzymes could be used.

It is possible to source MCT oils as starting materials to prepare the structured lipids useful in this invention. MCT oils, such as fractionated coconut oil and fractionated palm kernal oils, are obtained by the hydrolysis of coconut and palm kernel oils and the distillation of the fatty acids. The fatty acids are then re-esterified to the glycerol molecules to obtain the MCT oil.

The chemical interesterification process used for the preparation of the structured triglycerides in the following examples is according to the teachings found in the "Oils and Fats Manual, A Comprehensive Treatise", Vol. 2, Chapter 11, *Transformation of Fat for Use in Food Products*, pgs. 923–925, the entire teaching of which is hereby incorporated by reference.

If needed, an emulsifier of phospholipids, soybean, lecithin, milk, and other suitable sources may be added to the lipid blend to improved stability to the structured lipid blend.

It should be understood that the following are suitable sources for GLA, EPA, MCTs, and MUFAs in the lipid blend:

a) Sources of Omega 3 fatty acids: primarily fish oils (menhaden, salmon, tuna, sardine, herring, anchovy, mackerel, and others), as well as marine plankton, appropriate plant oils, linseed oil, fungal oils, and other suitable sources, as well as mixtures thereof;

b) GLA is available from borage oil (15–25% GLA), black currant oil (12–20%), evening primrose oil (8–10%), or other suitable sources, as well as mixtures thereof. DGLA can be synthesized de novo, or from GLA;

c) Omega 6 fatty acids (other than GLA & DGLA), plus Saturated fatty acids are available in the following oils: corn, cottonseed, soya, coconut, palm, soybean, walnut, and other suitable sources;

d) Monounsaturated, Omega 9 fatty acids (including, but not limited to, oleic acid, 18: 1n9), are available from the following oils: olive, canola, peanut, high oleic sunflower, high oleic safflower, avocados, pecans, almonds, hazel nuts, cashews, mustard seed, and other suitable sources;

e) MCTs are available in coconut, palm kernal, balassu, cohune, tucam and other suitable oils. Coconut is also high in lauric fatty acids;

f) Menhadin oil is high in caprylic (CS:0, 34%), capric (C10:0, 17%), EPA (14.5%), DHA (3.6%), and contains 22% Omega 3 fatty acids, 2–5% omega 6 fatty acids, and 1% linoleic acid. This oil, along with Borage oil (high in GLA), may be primary sources of EPA, DHA, GLA, Capric, Caprylic acids, while low in linoleic acid.

Furthermore, it should also be understood that the formula can include the following amino acids (preferably the "L" configuration thereof) per 240 calories of the formula:

a) L-Arginine about 1.0– to about 5.0 gm, preferably about 3.6– to about 4 gm;

b) L-Glutamine about 1.5– to about 7.5 gm, preferably about 3.0– to about 3.6 gm;

c) L-Proline about 1.0– to about 5.5 gm, preferably about 2.2– to about 2.7 gm;

d) Branched Chain Amino Acids (abbreviated BCAA), about 2.4– to about 9 gm/240 cal, preferably about 3.0– to about 4.0 gm; and e) Essential Amino Acids comprise about 30– to about 50%, (by weight) of amino acids, preferably about 35– to about 45%.

Citrulline and Ornithine may be used in place of Arginine, or any other suitable salt thereof. Glutamic acid and Glutamine are preferably mutually exclusive, although not absolutely necessary. BCAAs include, but are not limited to, 1-Leucine, 1-Isoleucine, and 1-Valine. Essential amino acids (EAAs) include, but are not limited to, the BCAAs plus L-Methionine, L-Phenylalanine, L-Tryptophan, L-Threonine, & L-Histadine. The weight distribution of the BCAAs should be fairly equal, with each amino acid not less than about 40% nor greater than 210% the weight of the other BCAAs. The weight of 1-leucine is preferred to be about 1.5:1–2.0:1 the weight of the other BCAAs.

The following is an exemplary formula:

L-Arginine (about 3.6 gm), L-Glutamine (about 3 gm), and L-Proline (about 2.4 gm) include only 3 of the non-essential amino acids (L-Alanine, L-Proline, Glycine, L-Serine, L-Tyrosine, L-Glutainine, L-Glutamic acid, L-Aspartic acid, L-Cysteine, L-Arginine), the total for these 3 amino acids is about 9 gm/240 cal It should be understood that this weight of L-Arginine, L-Glutamine, and L-Proline of about 9 gm, represents the majority of the non-essential amino acids, and thus dictates the requirement of essential amino acids. If about 35% –to about 45% (by weight) of total amino acids is Essential Amino Acids (EAAs), then the required weight of EAAs would be: if about 35%, about 4.8 gm, a minimum protein concentration of about 13.8 gm/240 cal; if about 40%, about 6.0 gm, a minimum protein concentration of about 15 gm/240 cal; if about 45%, about 7.5 gm, a minimum protein concentration of about 16.5 gm/240 cal.

It should be appreciated that the above values are minimum weights due to lack of including other non-essential amino acids, which would be included, as a matter of completeness.

The about 4.8 gm, 6.0 gm, or 7.5 gm of EAAs would include a desired concentration of about 3 gm BCAAs, leaving the remainder to non-Branched chain, essential amino acids. Depending upon the final weight of all EAAs, the BCAAs would be about 50– to about 80% of the final weight, preferably about 53%– to about 78%, or about 60% of final weight of EAAs.

Sources for protein include some free amino acids, plus hydrolyzed/whole proteins, including carob, whey, lactalbumin, egg albumin, milk, caseinates, soy, and mixtures thereof; high quality proteins, such as whey or lactalbumin are preferred, while whey is high in BCAAs, and carob is high in glutamine. Other suitable sources may also be used. The preferred protein system is primarily a hydrolysate. The hydrolysate is ideally administered in shorter peptide lengths, preferably 1–4 peptides, about 75–to about 85% (by number); 4–8 peptides, about 7–to about 14% (by number); 8–16 peptides, about 4–to about 8% (by number); and 16 or greater peptides, about <4%.

It should be appreciated that dipeptides, tripeptides, and quadrapeptides that include arginine, glutamine, proline and/or BCAAs is preferred over free amino acids.

The formula can also included carbohydrates, primarily maltodextrins or other similar sugar, with less than about 20%, preferably less than about 15%, sucrose and/or fructose. Indigestible carbohydrate: consisting of dietary fiber (pectin and/or gum Arabic), and/or indigestible oligosaccharides (fructooligosaccharides (FOS), and/or xylooligosaccharides can also be included. Concentration of indigestible carbohydrate: about 0.1–to about 9 gm per 240 cal, preferably about 3 gm/240 cal of the formula. Preferably, the formula is lactose free.

In addition, the formula can include minerals. The vitamins and minerals include the following:

a) Vitamin A, about 500–3300 IU, preferably about 1800–2200 IU, or even about 1990 IU, made up primarily of beta-carotene, with some alpha and gamma carotene, preferably natural versus synthetic;

b) Vitamin E-primarily natural d-alpha tocopherol (RRR isomer), about 10–160 IU, preferably about 80–100 IU. The formula may also contain about 20% gamma tocopherol, as well as a mixture of tocopherol and tocotrienols (alpha, beta, gamma and delta forms);

c) Vitamin C, preferably esterified/buffered, about 50–to about 800 mg, preferably about 240 mg;

d) Vitamin D, about 20– to about 250 IU, preferably about 100–to about 130 IU. Part of which may be made up of calcitriol;

e) Zinc about 2–to about 12 mg, preferably about 6.0 mg;

f) Selenium about 10–to about 135 mcg, preferably about 30 mcg;

g) Iron about 1.5–to about 7.5 mg, preferably about 4.5 mg, preferably ferrous fumarate;

h) Copper about 0.3–to about 0.75 mg preferably about 0.62 mg;

i) Vitamin B6 about 0.3–to about 25 mg, preferably about 10 mg;

j) Vitamin B12 about 1–to about 25 mcg, preferably about 10 mcg;

k) Folate (Folic Acid), about 50– to about 1000 mcg, preferably about 475 mcg;

l) Pantothenic acid, about 1.5–to about 700 mg, preferably about 100 mg;

m) Taurine, about 20–to about 500 mg, preferably about 125–to about 250 mg;

n) L-Carnitine, about 10–to about 1000 mg, preferably about 280 mg (L-carnitine, or equivalent in acetyl-1-carnitine);

o) Phosphorus about 100–to about 600 mg, preferably about 260–to about 300 mg p) Potassium about 300–to about 1000 mg, preferably about 500 mg;

q) Vitamin K about 5–70 mcg, preferably about 35–to about 40 mcg;

r) Manganese about 0.4–to about 2.9 mg, preferably about 0.8 mg, preferably aspartate and ascorbate salts;

s) Chromium about 10–to about 300 mcg, preferably about 72 mcg, possibly polynicotinate or picolinate salts, or as an organic salt;

t) Magnesium about 20– to about 300 mg, preferably about 100– to about 150 mg, preferably as Magnesium gluconate;

u) Calcium about 100– to about 400 mg, preferably about 200 mg, and preferably caseinate/citrate/malate/citrate-malate/phosphate tribasic salts;

v) Iodine about 10– to about 100 mcg, preferably about 42 mcg;

w) Molybdenum, about 10– to about 100 mcg, preferably about 42 mcg;

x) Fluoride, about 0.0–8 mg, preferably about 0.05 mg;

y) Vitamin B1 (thiamine), about 0.05– to about 105 mg, preferably about 10 mg;

z) Vitamin B2 (riboflavin), about 0.05– to about 1–5 mg, preferably about 10 mg;

aa) Vitamin B3 (niacin), about 5– to about 50 mg, preferably about 12 mg, preferably as nicotinamide/niacinamidel inositol hexanicotinate;

bb) Biotin about 50– to about 1000 mcg, preferably about 500 mcg;

cc) Choline about 50– to about 5000 mg, preferably about 1500 mg, as free base or with pharmacologically equivalent precursors/derivatives (lecithin, phosphatidylcholine)

dd) Inositol about 50– to about 1000 mg, preferably about 240 mg;

ee) Lutein about 0.0– to about 5 mg, preferably about 1 mg;

ff) Lycopene about 0.0– to about 5 mg, preferably about 1 mg;

gg) Cholesterol about 0.0– to about 100 mg, preferably about 40 mg;

hh) Appropriate amounts of sodium and chloride. Sodium to range from about 50– to about 900 mg, preferably about 225 mg, and chloride to range from about 50– to about 900 mg, preferably about 275 mg; and ii) May contain trace amounts of Vanadium, Cobalt, Cadmium, Tin, Nickel, Boron, Silver.

Although the formula is designed per 240 calories, concentration adjustments will be appropriate for renal and/or hepatic failure, and/or severely fluid restricted patients.

Preferably no carbonate salts are included in the formula. Gluconate salts may work well, as well as some dibasic/tribasic phosphate salts. Amino acid chelates are also an option (to enhance absorption, decrease diarrhea side effects). Ascorbates, maleates, and citrates may also be suitable salts.

It should also be appreciated that the formula can include RNA/DNA. Sources for RNA/DNA may include yeast, or other suitable sources. The dose of RNA equivalents is about 10– to about 3000 mg/240 calories of formula, preferably about 250– to about 900 mg, most preferably about 650 mg. To enhance the absorption of RNA/equivalents, while decreasing the diarrhea associated with such supplementation, acyl derivatives with arginine, glutamine, proline, BCAAs, choline, alpha lipoic acid, glycine and other suitable ligands are preferred. It should also be understood that, in reference to amino acids, the usage of glycine may be preferred since it is the smallest amino acid and has the least steric hindrance.

Furthermore, it should be appreciated that minerals can be included in the formula. Minerals include, but are not limited to, iron, copper, zinc, manganese, copper, vanadium, calcium, iodine, molybdenum, flouride, selenium, tin, nickel, silver, boron, magnesium, and chromium.

In addition it should be appreciated that metal protein complexes/chelates may be used to improve absorption of metal and the amino acid/protein ligand, these amino acids include, but are not limited to, arginine, glutamine, proline, BCAAs, and glycine.

The usage of chelates and/or complexes improves the absorption of both ligands, and thus their effectiveness, and also decreases their gastrointestinal side effects.

In addition, the formula may contain Pyruvate, preferably in the form of a Pyruvyl-amino acid in which the preferred amino acid is arginine and/or glutamine. Other possible amino acids include proline, BCAAs, and any di-/tri-/poly-peptide linkage.

With respect to pyruvate the dose per 240 calories is about 2– to about 25% of total calories, preferably about 5– to about 15%, most preferably about 10%. It should be appreciated that "calories dose" of pyruvate is taken out of the total allowed carbohydrate calories. Thus, the total carbohydrate calories are unchanged.

The formula can also include:

a) Pycnogenol, or closely related compounds, about 0.1– to about 90 mg, preferably about 12 mg;

b) Alpha-Lipoic acid about 0.1– to about 450 mg, preferably about 125 mg. Alpha-lipoic acid may also be referred to as thioctic acid, 1,2-dithiolane-3-pentanoic acid, 1,2-dithiolane-3 valeric acid, and 6,8-dithiooctanoic acid, and alpha lipoate;

c) Oxerutins [0-(beta-hydroxyethyl)-rutosides, including trihydroxyethylrutoside, monohydroxyethylrutoside, dihydroxyethlrutoside, and tetrahydroxyethylrutoside] about 10– to about 850 mg, preferably about 225 mg. Oxerutins is preferred; an alternative is Horse Chestnut Extract {triterpene glycosides (Escin)}, at a concentration of about 5– to about 750 mg, preferably about 145 mg. (Horse Chestnut Extract eliminates the toxin associated with the whole chestnut; the toxin is primarily aesculin.)

d) Coenzyme Q10 (ubiquinone), about 5– to about 300 mg, preferably about 40 mg e) N-acetyl-cysteine ("NAC"), about 0.1– to about 1000 mg, preferably about 375 mg It should be appreciated that the formula can be based upon concentrations/240 calories, and thus is adaptable to various caloric concentrations (0.6 kcal/ml–3 kacl/ml), although for some of the higher concentrations used, changes in electrolyte concentrations may be made due to their use in acute/chronic renal failure, and/or severe hepatic failure.

The following breakdowns for caloric concentrations of protein, carbohydrate, and fat are exemplary in nature.

| Caloric Concentration (cal/ml) | Caloric Percent Protein | Caloric Percent Carbohydrate | Caloric Percent Fat |
|---|---|---|---|
| 1.01 Range: | 16–28% | 45–70% | 12–33% |
| Preferred: | 20–25% | 48–55% | 25–29% |
| 0.5 Range: | 18–26% | 36–44% | 38–42% |
| Preferred: | 20–25% | 38% | 40% |
| 1.01 Range: | 14–22% | 39–45% | 39–45% |
| Preferred Higher Fat | 17–20% | 40–43% | 40–43% |
| | | | |
| 1.01 Range: | 16–25% | 34–40% | 40–49% |
| Preferred: Higher Fat | 18–22% | 35–37% | 43–45% |
| | | | |
| 1.5 Range: | 13–22% | 26–39% | 40–60% |
| Preferred: | 15–19% | 27–29% | 52–55% |
| Concentrated, 2.0 With low electrolytes & normal protein | 5–18% 6–16% (*and other suitable additive reductions) | 48–52% 49–51% | 40–45% (Range) 40–43% (Preferred) |
| Concentrated, 2.0 With low electrolytes & decreased protein | 5–12% 6–10% (*and other suitable additive reductions) | 48–52% 49–51% | 40–45% (Range 40–43% (Preferred) |

Please also note that neither NAC nor RNA/DNA/equivalents thereof are figured into the calories provided. Pyruvate, if included, is part of total carbohydrate calories.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected.

The invention claimed is:

1. A formulation for enteral administration to a patient, comprising:
   from about 1 gram to about 5 grams of Arginine per 240 calories of said formulation;
   from about 1.5 grams to about 7.5 grams of Glutamine per 240 calories of said formulation;
   from about 1 gram to about 5.5 grams of Proline per 240 calories of said formulation;
   from about 2.4 grams to about 9 grams of branched chain amino acids per 240 calories of said formulation; and
   from about 10 milligrams to about 3 grams of RNA or an acyl-RNA per 240 calories of said formulation.

2. The formulation of claim 1, wherein said acyl-RNA is selected from the group consisting of argininyl-RNA, glutaminyl-RNA, prolyl-RNA, glycyl-RNA, branched chain amino acid-RNA, and alpha-lipoic acid-RNA.

3. A formulation for enteral administration to a patient, comprising:
   from about 1 gram to about 5 grams of Arginine per 240 calories of said formulation;
   from about 1.5 grams to about 7.5 grams of Glutamine per 240 calories of said formulation;
   from about 1 gram to about 5.5 grams of Proline per 240 calories of said formulation;
   from about 2.4 grams to about 9 grams of branched chain amino acids per 240 calories of said formulation; and
   from about 2% to about 25% of total calories as pyruvate, a pyruvyl-amino acid, or a pyruvyl-peptide per 240 calories of said formulation.

4. The formulation of claim 3, wherein said pyruvyl-peptide is selected from the group consisting of pyruvyl-dipeptide, pyruvyl-tripeptide, and pyruvyl-polypeptide.

5. The formulation of claim 3, wherein said pyruvyl-amino acid is selected from the group consisting of pyruvyl-arginine, pyruvyl-glutamine, pyruvyl-proline, and pyruvyl-branched chain amino acids.

6. A formulation for enteral administration to a patient, comprising:
   Pycnogenol, Alpha-Lipoic acid, Oxerutin or a triterpene glycoside, Coenzyme Q10, N-acetyl-cysteine, and RNA or an acyl-RNA.

7. The formulation of claim 6, wherein said acyl-RNA is selected from the group consisting of argininyl-RNA, glutaminyl-RNA, prolyl-RNA, glycyl-RNA, branched chain amino acid-RNA, and alpha-lipoic acid-RNA.

8. A formulation for enteral administration to a patient, comprising:
   Pycnogenol, Alpha-Lipoic acid, Oxerutin or a triterpene glycoside, Coenzyme Q10, N-acetyl-cysteine, and a pyruvyl-amino acid, or a pyruvyl-peptide.

9. The formulation of claim 8, wherein said pyruvyl-peptide is selected from the group consisting of pyruvyl-dipeptide, pyruvyl-tripeptide, and pyruvyl-polypeptide.

10. The formulation of claim 8, wherein said pyruvyl-amino acid is selected from the group consisting of pyruvyl-arginine, pyruvyl-glutamine, pyruvyl-proline, and pyruvyl-branched chain amino acids.

11. A formulation for enteral or oral administration to a patient comprising:
   Arginine, Glutamine, Proline, branched chain amino acids, pyruvate, a pyruvyl-amino acid, or a pyruvyl-peptide, RNA or an acyl-RNA, Coenzyme Q10, N-acetyl-cysteine, and Alpha-Lipoic acid.

12. A method of providing nutrition to a patient in need thereof, the method comprising:
   enterally administering to the patient a formulation having from about 1 gram to about 5 grams of Arginine per 240 calories of said formulation;
   from about 1.5 grams to about 7.5 grams of Glutamine per 240 calories of said formulation;

from about 1 gram to about 5.5 grams of Proline per 240 calories of said formulation; and from about 2.4 grams to about 9 grams of branched chain amino acids per 240 calories of said formulation.

13. The method of claim 12, wherein:

said enterally administering includes orally administering the formulation to the patient.

14. The method of claim 12, wherein:

said formulation further includes RNA or an acyl RNA.

15. The method of claim 12, wherein:

said formulation further includes pyruvate, a pyruvyl-amino acid, or a pyruvyl-peptide.

16. A method of providing nutrition to a patient in need thereof, the method comprising:

enterally administering to the patient a formulation having Pycnogenol, Alpha-Lipoic acid, Oxerutin or a triterpene glycoside, Coenzyme Q10, and N-acetyl-cysteine.

17. The method of claim 16, wherein:

said enterally administering includes orally administering the formulation to the patient.

18. The method of claim 16, wherein:

said formulation further includes RNA or an acyl-RNA.

19. The method of claim 16, wherein:

said formulation further includes pyruvate, a pyruvyl-amino acid, or a pyruvyl-peptide.

* * * * *

UNITED STATES PATENT AND TRADEMARK OFFICE
CERTIFICATE OF CORRECTION

| | | |
|---|---|---|
| PATENT NO. | : 7,196,065 B2 | Page 1 of 1 |
| APPLICATION NO. | : 10/992985 | |
| DATED | : March 27, 2007 | |
| INVENTOR(S) | : Stephen P. Ernest | |

It is certified that error appears in the above-identified patent and that said Letters Patent is hereby corrected as shown below:

Column 10, line 46, please insert --pyruvate,-- after the word "and".

Signed and Sealed this

Twenty-second Day of May, 2007

JON W. DUDAS
*Director of the United States Patent and Trademark Office*